| United States Patent [19]
LaRocca et al.

[11] Patent Number: 5,158,940
[45] Date of Patent: Oct. 27, 1992

[54] USE OF SURAMIN TO TREAT RHEUMATOLOGIC DISEASES

[75] Inventors: Renato V. LaRocca, Sterling, Va.; Cy A. Stein, Gaithersburg, Md.; Michael R. Cooper, Gaithersburg, Md.; Charles E. Myers, Rockville, Md.

[73] Assignee: The United States Government as represented by the Secretary, DHHS, Washington, D.C.

[21] Appl. No.: 479,817

[22] Filed: Feb. 14, 1990

[51] Int. Cl.$^5$ ............................................. A61K 31/715
[52] U.S. Cl. ........................................................ 514/54
[58] Field of Search .......................................... 514/54

[56] References Cited
PUBLICATIONS

Horne et al, Blood vol. 71. (2) pp. 273-279 (1988).
Mohan et al, Journal of Medicinal Chemistry 34(1) pp. 212-217 (1991).
Akerpelpt et al, Journal of Medicinal Chemistry vol. 14(7) (1971).

Primary Examiner—S. J. Friedman
Attorney, Agent, or Firm—John E. Tarcza

[57] ABSTRACT

Polysulfonated compounds such as suramin are used to treat immunoregulatory disorders. Particular use in the treatment of rheumatologic diseases such as rheumatoid arthritis is shown.

11 Claims, 3 Drawing Sheets

USE OF SURAMIN TO TREAT RHEUMATOLOGIC DISEASES

BACKGROUND OF THE INVENTION

Rheumatoid arthritis is a chronic debilitating disease which is believed to be autoimmune in nature. While many drugs have been used to treat it with varying degrees of clinical benefit, numerous side effects and toxicities often accompany the treatment. Furthermore, the long term effect of these medications on rheumatoid arthritis remains controversial in as much as some patients require medication for life while many others have periodic episodes of recrudescence and remission or become progressively worse despite drug therapy. Drug treatments typically include nonsteroidal anti-inflammatory drugs, hydroxychloroquin, gold salts, steroids, methotrexate and penicillamine. Much the same can be said for all autoimmune diseases, especially those believed to be influenced by the cellular immune response.

Suramin, the hexasodium salt of 8,8'-(carbonyl-bis-(imino-3,1-phenylenecarbonylimino(4-methyl-3,1-phenylene)carbonylimo))bis-1,3,5-naphthalenetrisulfonic acid is a polysulfonated napthtylurea which has found clinical use as an antiparasitic agent since the 1920s. It has a long plasma half-life of 45-55 days. African trypanosomiasis and onchocerciasis are usually treated with suramin. It has also been tested as a possible treatment for acquired immunodeficiency syndrome (AIDS), because of its ability to inhibit the reverse transcriptase enzyme and revert the cytopathic effect of human immunodeficiency virus (HIV) in vitro (JAMA 258 p. 1347-51 (1987)). Suramin also has demonstrated an ability to inhibit the activity of various growth factors in vitro (J. Cellular Physiology 132 p. 143-8 (1987)) and has therefore been used clinically to treat various cancers. The compound has also been noted to bind to a variety of cytoplasmic and intranuclear enzymes (Cancer Res. 47 p. 4694-8 (1987) and J. CLin. Onc. 7 p. 499-508 (1989)) but the exact mode of its action is still not fully understood.

In recent years, people have attempted to use suramin and related compounds for several other purposes such as a collagenase inhibitor and for inhibition of the complement activators associated with angioneurotic edema (Quinke's Disease) (U.S. Pat. Nos. 4,591,604, 4,391,824, 4,297,372, and 4,180,587). While these same patents have speculated on the use of suramin to treat rheumatoid arthritis and related diseases, no evidence has ever been presented that suramin effectively has any activity against any autoimmune disorder. Recent patents and publications show the opposite and use suramin as an immunostimulant (U.S. Pat. No. 4,737,521 and the AIDS and cancer treatments citations above) instead of as an immunosuppressant.

Historically, treatment with suramin has been attempted in numerous other diseases and many reports of its use have been suggested. However, these appear to be no more than desperation attempts to treat patients with then otherwise incurable diseases by any means available, and without success. Similar desperation attempts have been tried with any of a wide assortment of drugs prior to FDA regulation and the advancements of recent decades.

Suramin has only one approved dosage and treatment protocol-namely using one gram bolus doses given parenterally once per week for six weeks for a total dose of six grams to treat parasitic infections. This protocol is generally effective for treating parasitic infections.

SUMMARY OF THE INVENTION

The inventors have discovered that rheumatoid arthritis and other immunoregulatory diseases are effectively treated using suramin and related polysulfonated compounds and their pharmaceutically acceptable salts. Further, it has been discovered that much higher doses are needed to produce the anti-autoimmune effect than are needed to treat parasitic infections. Doses at this level require frequent pharmacological analysis of the serum level in as much as levels over 350 ug/ml are neurotoxic and have a 40% chance of causing reversible paralysis.

DETAILED DESCRIPTION OF THE INVENTION

Figure 1A:
FIG. 1A shows the right hand of a patient at the start of treatment.
Figure 1B:
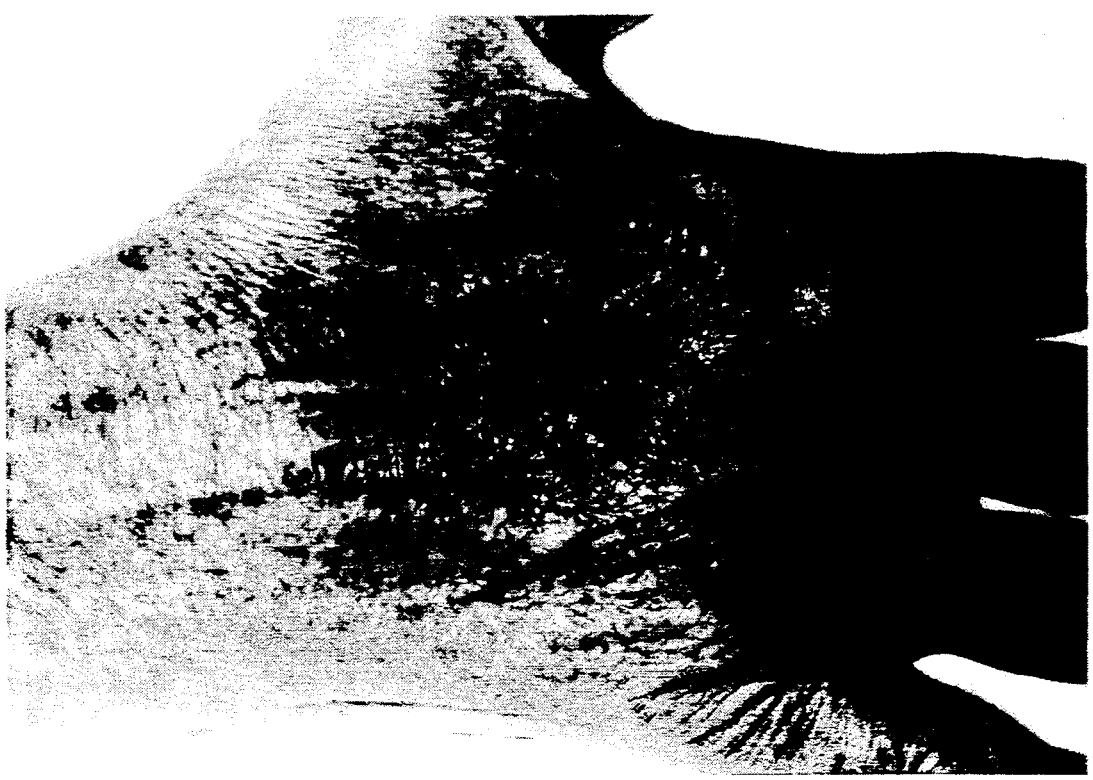
FIG. 1B shows the right hand of the same patient after seven months of treatment.
Figure 2A:
FIG. 2A shows the elbows of a patient at the start of treatment.
Figure 2B:
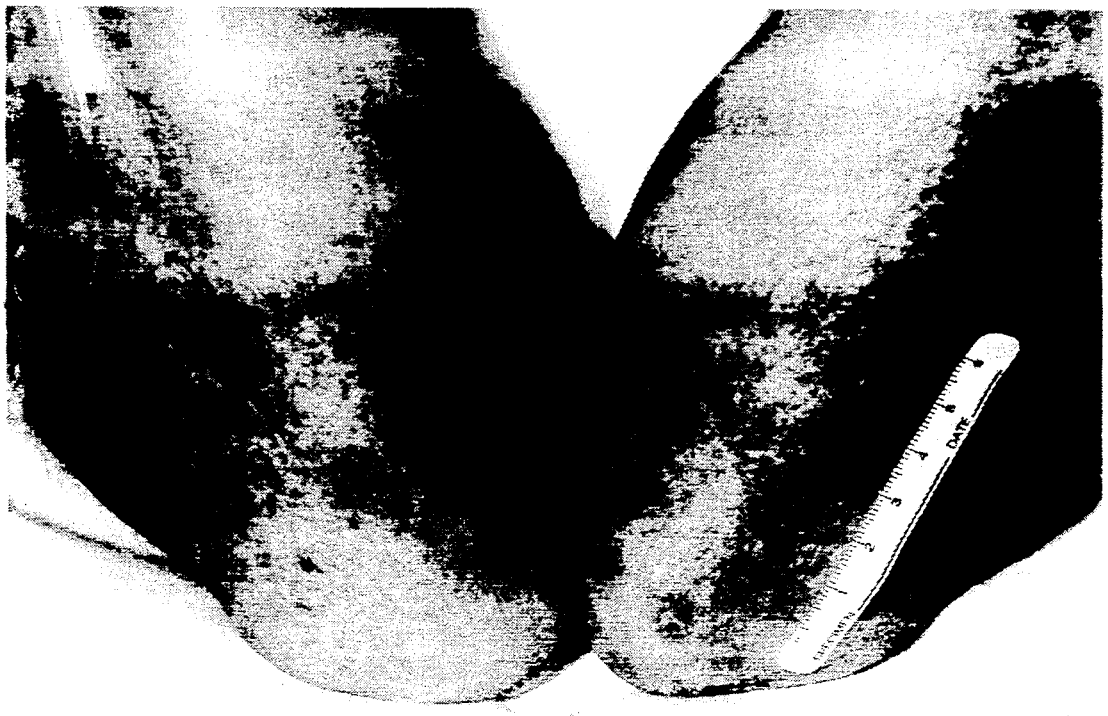
FIG. 2B shows the elbows of the same patient after seven months of treatment.
Figure 3:
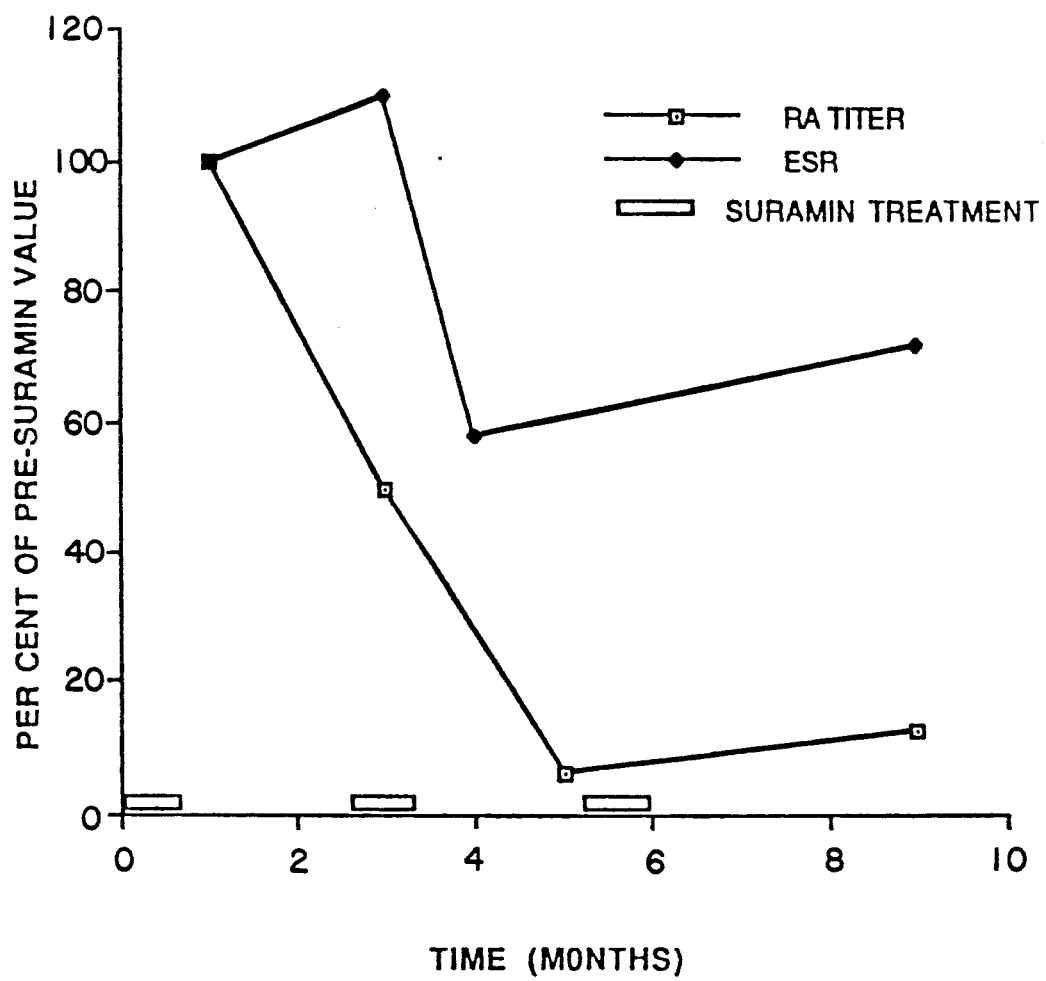

Patients suffering from immunoregulatory diseases such as autoimmune diseases requiring immunomodulation may be treated with a number of polysulfonated organic compounds, especially those containing sulfonated ring systems. These therapeutic compounds include heparin sulfate, dextran sulfate, polysulfonated glycosaminoglycans and suramin. While not wishing to be bound by any particular theory, these compounds are believed to have agonist/antagonist properties on various cell growth factors, cytokines, and may even unbind those already bound to cellular or other receptors. These compounds are believed to function by suppressing the immune system through interference with the activity of various growth factors and cytokines. This may result in blockage of the mitogenic proliferation of the cellular immune system, which is responsible for causing the disease state. A variety of immunological disorders, especially those operating by analogous mechanisms, are treatable in accordance with the invention. The particular autoimmune and allergic diseases include Crohn's disease, ulcerative colitis, sarcoidosis, rheumatoid arthritis, scleroderma, polyarteritis, psoriasis, interstitial and glomerular nephrites, systemic lupus erythematosus, polymyositis, Sjogren's syndrome, asthma and other inflammatory alveolar disorders. Rheumatologic disorders are the preferred diseases to treat according to the invention.

When treating a patient, the dose and protocol for administrating it differs from the conventional way of using suramin. While the approved protocol for using suramin is a one gram bolus dose given once a week for six weeks for a total dose of six grams, the treatment of rheumatologic diseases involves generating a much higher plasma level of suramin and maintaining it for a longer period of time. Typically, about 10 to 30 grams, preferably greater than about 15 grams total dose, are given over a period of several months and may be given in about one to about three week periods of therapy. During the treatment period it is preferred to maintain a plasma level from about 100 to about 350 ug/ml, preferably above 200 ug/ml and more preferably above 300 ug/ml. Since levels above 350 ug/ml are potentially neurotoxic, the patient should be frequently monitored to ensure that the plasma levels are within the desired range. The treatments may be repeated or maintained as long as necessary. Comparable doses of the other active compounds of the invention would be determined by routine optimization.

The therapeutic compounds of the invention may be given orally except for when plasma levels are not achieved by this route due to poor adsorption or degradation in the digestive tract. For these situations, parenteral administration is preferred. The compounds may also be provided transdermally or adsorbed through one or more of the mucus membranes. The drug may be given in one or more bolus doses or it may be given by continuous infusion. In general, a suitable initial continuous infusion rate of about 350 mg/m$^2$/day for suramin may be used. A desired dose may also be provided in several increments at regular intervals throughout the day or sustained release formulations. The doses will need to be modified according to the condition of the patient and his ability to tolerate the side effects, his clinical needs and the nature of whatever other treatment is being employed. Any of the standard pharmaceutical stabilizers, carriers, salts and preparations used with other conventional drugs may also be used for the preparation and delivery of suramin.

The desired plasma level may be achieved, for example, by intravenous injection of 0.1% to 50%, preferably about 10%, concentration in solution of the active ingredient.

Formulations for transdermal administration include a suitable carrier such as a cream or base of other material to facilitate contact with the skin or mucus membranes. The active ingredient(s) contained therein may be charged, or converted into a salt in order to permit crossing the surface under the influence of an electrical field. Alternatively, the active ingredient may be derivatized in order to enhance absorption or transport across the cell layer.

The compounds of the invention in either a fine powder or liquid form with suitable carriers as needed may be aerosolized for inhalation to deliver the compounds.

Formulations for administration to a mucus membrane surface may be presented with a suitable carrier or salt of inert ingredients to aid in contact or absorption or the active compounds. Such carriers as are known in the art to be appropriate.

Formulations suitable for parenteral administration include aqueous and non-aqueous, isotonic and isosmotic sterile injection solutions which may contain antioxidants, buffers, bacteriostats, and solutes which render the formulation isotonic with the body fluids of the intended recipient and aqueous and non-aqueous sterile suspensions which may include suspending agents and thickening agents. The formulations may be presented in unit-dose or multi-dose sealed containers, such as ampules and vials, and may be stored in a freeze-dried (lyophilized) condition requiring only the addition of the sterile liquid carrier (e.g. water, saline) for injection immediately prior to use. Extemporaneous injection solutions and suspensions may be prepared from powders, granules and tablets of the kind previously described. In all cases, the final product is preferably free of pyrogens.

In vitro assays and even animal testing has its merits but neither stands up perfectly in drug testing and hence the need for human trials to prove efficacy. This is particularly true for immunoregulatory and autoimmune diseases where the nature of the disease mechanism is unclear and animal models are imperfect. Because suramin is already an FDA approved drug, is well known and has been used for seventy years, it was the logical choice for use in clinical trials. As for the disease to treat, rheumatoid arthritis is a well known autoimmune disease which is objectively quantifiable by measuring the titer of rheumatoid factor, the shrinkage and disappearance of rheumatoid nodules, and the diminution of joint inflammation. Further, subjective patient reports of pain stiffness and other arthritic symptoms are most important but are not available with either in vitro or animal models. Accordingly, the following representative example is presented.

EXAMPLE

A 57 year old Caucasian male was initially diagnosed in 1975 with polyarthritis and an elevated serum rheumatoid factor level. Since then, the patient had required almost uninterrupted treatment with either supraphysiologic doses of steroid or remission-inducing agents. These included hydroxycloroquine, gold salts, cytoxan and most recently, penicillamine together with prednisone. Tapering of these invariably resulted in exacerbation of his arthritic symptoms.

Prior to initiating suramin therapy, penicillamine and prednisone were discontinued and the patient was placed on physiologic replacement doses of hydrocortisone. At this time, the patient demonstrated synovial proliferation of the metacarpophalangeal joints of both hands, osteopenia and diffuse biopsy proven rheumatoid nodules involving the thenar aspect of both forearms, the dorsum of each hand as well as along his left achilles tendon. His serum rheumatoid factor titer was 1:2560. Serum antinuclear antibodies were absent and both anti-DNA screen and LE cell test were negative.

Over six and one half months, the patient received three cycles of suramin by continuous infusion at eight week intervals, for a cumulative dose of 23.4 grams. In this period the patient did not experience any significant hematologic, hepatic or renal toxicity. Over the same period plus an additional three months afterwards without suramin treatment, the patient manifested decreased synovial swelling and improvement in his arthritic symptoms. In addition, regression in the size of his multiple rheumatoid nodules occurred; this was initially documented after three months and was even more pronounced at the start of the third cycle of therapy at five months with the complete disappearance of as many as a third. Although a follow up hand photograph failed to show any significant change in his minimal joint abnormalities, the patient's serum rheumatoid titer fell to 1:1280 after three months and 1:160 after six months. Upon formal rheumatologic evaluation at the end of therapy, the patient showed virtually no inflammatory joint disease with only minimal synovial proliferation in the ulnar carpal region of his right wrist. The patient did not receive further treatment with suramin subsequent to his third cycle at six months, and by nine months after the initial start continued to remain without arthritic symptoms, although his rheumatoid titer has increased to 1:320. The size of his remaining rheumatoid nodules at this time also remained unchanged.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Other modifications of the above embodiments of the invention which are obvious to those skilled in the art or are within the invention's true spirit and scope are intended to be within the scope of the following claims.

We claim:

1. A method for treating immunoregulatory or autoimmune diseases by administering to a patient an immunomodulating amount of suramin or a salt thereof.

2. A method for treating rheumatologic diseases by administering to a patient an effective amount of suramin or a salt thereof.

3. The method of claim 2 further comprising administering suramin or a salt thereof by continuous infusion.

4. The method of claim 2 further comprising maintaining serum levels between about 100 and about 350 ug/ml.

5. The method of claim 2 further comprising maintaining serum levels above 300 ug/ml.

6. The method of claim 2 further comprising maintaining serum levels of suramin or a salt thereof for at least four months.

7. The method of claim 6 wherein said levels are maintained for at least 8 months.

8. A method for treating rheumatoid arthritis comprising administering suramin or a salt thereof to a patient for sufficient duration and at sufficient dosage to alleviate the signs and symptoms of rheumatoid arthritis.

9. The method of claim 8 wherein the signs and symptoms remain alleviated for at least three months after finishing treatment.

10. The method of claim 8 further comprising maintaining the serum levels of suramin or a salt thereof above about 100 ug/ml.

11. The method of claim 8 further comprising maintaining the serum levels of suramin or its salts below about 350 ug/ml.

* * * * *